United States Patent [19]

Siemensmeyer et al.

[11] Patent Number: 5,753,141
[45] Date of Patent: May 19, 1998

[54] CHIRAL COMPOUNDS

[75] Inventors: Karl Siemensmeyer, Frankenthal; Volkmar Vill; Hanns-Walter Tunger, both of Hamburg, all of Germany

[73] Assignee: BASF Aktiengesellschaft, Ludwigshafen, Germany

[21] Appl. No.: 704,605

[22] PCT Filed: Mar. 9, 1995

[86] PCT No.: PCT/EP95/00866

§ 371 Date: Sep. 16, 1996

§ 102(e) Date: Sep. 16, 1996

[87] PCT Pub. No.: WO95/25150

PCT Pub. Date: Sep. 21, 1995

[30] Foreign Application Priority Data

Mar. 15, 1994 [DE] Germany .......................... 44 08 804 3

[51] Int. Cl.$^6$ .......................... C09K 19/32; C09K 19/34; C09K 19/30; C07D 493/04
[52] U.S. Cl. .......................... 252/299.62; 252/299.61; 252/299.63; 549/364
[58] Field of Search .......................... 252/299.01, 299.62, 252/299.61, 299.63; 549/364

[56] References Cited

FOREIGN PATENT DOCUMENTS

| | | |
|---|---|---|
| 38 27 603 A1 | 8/1988 | Germany . |
| 39 17 196 A1 | 5/1989 | Germany . |
| 39 30 667 A1 | 9/1989 | Germany . |

OTHER PUBLICATIONS

Mol.Cryst. . . . Liq. Cryst.,, 1984, vol. 114, pp. 151–187.
Ferroelectrics, 1990, vol. 104, pp. 241–256.

*Primary Examiner*—Shean C. Wu
*Attorney, Agent, or Firm*—Oblon, Spivak, McClelland, Maier & Neustadt, P.C.

[57] ABSTRACT

The invention relates to chiral compounds of the general formula

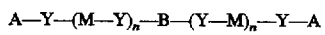

where

B is a radical of the formula

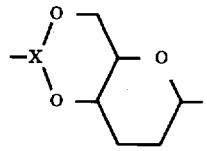

or

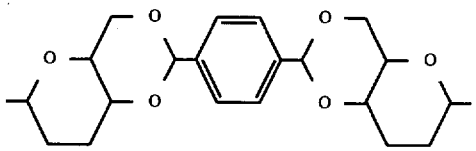

and where the radicals

A independently of one another are $C_1$- to $C_{20}$-alkyl which may be substituted by fluorine, chlorine, bromine or cyano and may be interrupted by O, S, NH, $NCH_3$, COO or OCO, X are carbon or boron, Y independently of one another are a chemical bond, O, S, NH, $N(CH_3)$, COO or OCO and M independently of one another are a mesogenic group and n independently of one another are 0 or 1 with the proviso that one n is other than 0.

The compounds according to the invention are suitable as dopes in liquid-crystalline media.

6 Claims, No Drawings

CHIRAL COMPOUNDS

This application is a 371 of PCT/EP45/00866, filed on Mar. 9, 1995.

Chiral, smectic, liquid-crystalline materials which on cooling from the liquid-crystalline phase solidify in a glass-like manner with formation of a layer structure are employed for many purposes, as is known, in the electrooptical field. Examples which may be mentioned here are optical storage systems (DE-A-3 827 603 and DE-A-3 917 196), electrophotography (DE-A-3 930 667), liquid-crystalline display elements such as displays (Mol. Cryst. Liq. Cryst., 114, (1990) 151) and also, in the case of simultaneously present ferroelectric behavior, electrical storage systems Ferroelectrics, 104, (1990) 241).

In the layer structure of ferroelectric $S_c^*$ phases, the molecular long axes are inclined within the individual layer to the layer perpendiculars z. The direction of this inclination is given by the director n; the angle between z and n is the tilt angle $\Theta$. $S_c^*$ phases exhibit two stable states having a different direction of n, which can be switched between by applying an electric field (electrooptical effect).

$S_c^*$ phases occur in low-molecular-weight, liquid-crystalline materials, in oligomesogens and in polymeric ferroelectric materials, the essential properties of the $S_c^*$ phases agreeing.

The liquid-crystalline materials prepared until now, however, have disadvantages, for example low spontaneous polarization, low phase width, no stable, tilted smectic glass at room temperature or excessively slow switching.

The occurrence of the liquid-crystalline $S_c^*$ phase is affected to a considerable extent by all groups of the molecule, ie. side group A, mesogenic group M and the chiral group, such that the smallest changes in the molecular structure can induce $S_c^*$ phases or cause them to disappear.

The chiral group especially is of crucial importance for the achievement of spontaneous polarization, due to its structure and special function.

The present invention is based on the object of finding chiral groups for liquid-crystalline materials which affect the liquid-crystalline properties as little as possible, simultaneously induce high spontaneous polarizations and are synthetically accessible.

The invention therefore relates to compounds of the general formula I

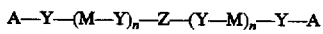

where
Z is a radical of the formula

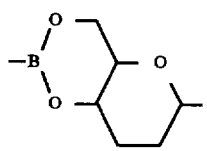

or

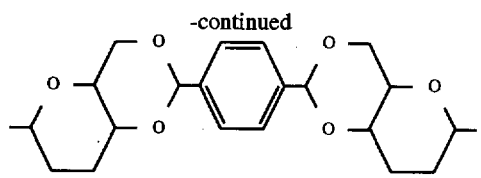

and where the radicals

A independently of one another are $C_1$- to $C_{30}$-alkyl which may be substituted by fluorine, chlorine, bromine or cyano and may be interrupted by O, S, NH, $NCH_3$, COO or OCO, Y independently of one another are a chemical bond, O, S, NH, $N(CH_3)$, COO or OCO and M independently of one another are a mesogenic group consisting of an aromatic or aliphatic ring system of the general formula II

where the radicals $Y^1$ independently of one another are a direct bond, O, COO, OCO, $CH_2O$, $OCH_2$, CH=N or N=CH, $Z^1$ independently of one another are p-phenylene, 1,3,4-thiadiazol-2,5-ylene or 2,5-pyrimidylene which may be substituted by fluorine, chlorine, bromine, iodine, cyano, hydroxyl, methoxy or methyl, and m is an integer from 1 to 3,
and n independently of one another are 0 or 1 with the proviso that one n is other than 0.

The invention particularly relates to compounds of the general formula I where the radicals A independently of one another are $C_1$- to $C_{20}$-alkyl, preferably $C_6$- to $C_{14}$-alkyl, which may be interrupted by O, COO or OCO, Y independently of one another are a direct bond or O, COO or OCO.

The use of the compounds according to the invention for the construction of recording layers for laser optical and electrical recording elements, in electrophotography, for the production of latent charge images, for the construction or as a component of liquid-crystalline display elements and also as colored reflectors is likewise a subject of the invention.

The mesogenic molecular moiety M consists of an aromatic or aliphatic ring system of the general formula II

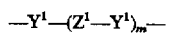

where the radicals $Y^1$ independently of one another are a direct bond, O, COO, OCO, $CH_2O$, $OCH_2$, CH=N or N=CH, $Z^1$ independently of one another are p-phenylene, 1,3,4-thiadiazol-2,5-ylene or 2,5-pyrimidylene which may be substituted by fluorine, chlorine, bromine, iodine, cyano, hydroxyl, methoxy or methyl, and m is an integer from 1 to 3.

Examples of particularly preferred $Z^1$ groups are

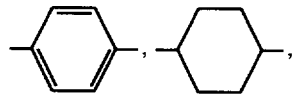

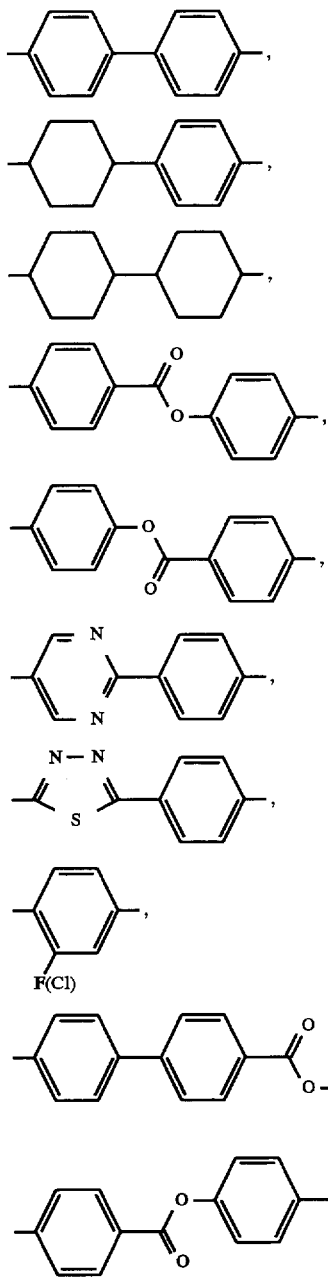

The units A—Y—(M—Y)$_n$ according to the invention, where A, Y and M have the meaning indicated above, are accessible in principle by generally known synthesis processes, as are described eg. in DE-A-3 917 186 and in Mol.Cryst.Liq.Cryst.191, (1991) 231.

All reactions were monitored by thin-layer chromatography (TLC) on silica gel ready-to-use film GF 254 (Merck). Detection was carried out by UV fluorescence quenching and/or spraying with 15% strength ethanolic sulfuric acid and subsequent heat treatment.

Column chromatography separations were carried out by flash chromatography on silica gel 60 (230–400 mesh, Merck).

The measurements of the optical rotations were carried out using a Perkin-Elmer polarimeter 589 (sodium D line).

The NMR spectra ($^1$H: 400 HMz, $^{13}$C: 100.67 MHz) were measured in the service unit on a Bruker AMX-400 NMR spectrometer. Analysis was carried out according to first order.

The phase transition temperatures were determined using a Leitz polarization microscope (Ortholux II pol) in combination with a Mettler microscope hot stage (Mettler FP 800/84). The following abbreviations were used throughout for indicating the phases (chiral phases are indicated by *):

K crystalline phase,
$S_C$ smectic C phase
$S_A$ smectic A phase
Ch cholesteric phase
I isotropic liquid phase
D cubic D-phase
Q smectic Q-phase General working procedures Preparation of the phenyl ethers (procedure 1)

25 mmol of the phenol are dissolved in ml of acetone, and the solution is treated with 50 mmol of the alkyl halide and 30 mmol (4.14 g) of potassium carbonate and boiled under reflux until all the phenol has reacted. The acetone is stripped off on a rotary evaporator and the residue is distilled in vacuo.

Reaction of the C-glycosides with boronic acids (procedure 2)

10 mmol of β-glycoside are taken up in 4 ml of toluene and treated with 20 mmol of the boronic acid. By stripping off the solvent several times on a rotary evaporator in vacuo, the water formed in the reaction is azeotropically distilled off with the toluene. The crystalline residue is recrystallized from ethanol.

Transacetalization of dimethyl acetals with C-glycosides (procedure 3)

8 mmol of the β-glycoside are dissolved in 4 ml of absolute dimethylformamide with 9.6 mmol of the dimethyl acetal and a spatula tipful of p-toluenesulfonic acid and the mixture is reacted on a rotary evaporator at a water bath temperature of 69°–65° C. and a pressure of 29–33 hPa. After the end of the reaction, the solvent is stripped off and the residue is treated after crystallization with a few ml of saturated sodium hydrogen carbonate solution, filtered off, washed with water and cold ethanol and recrystallized from ethanol.

EXAMPLE 1

Preparation of (1S,3R,6R,8R)-(4"-decyloxyphenyl)-8-(4'-decyloxyphenyl)-2,4,7-trioxybicyclo[4.4.0]decane

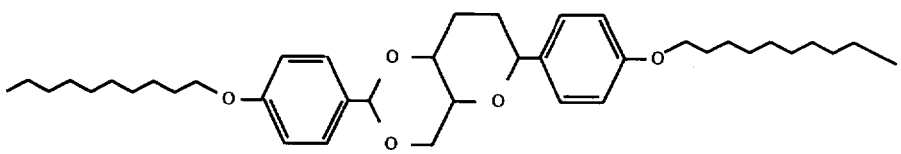

a) Preparation of 1'-(4,6-di-O-acetyl-2,3-dideoxy-β-D-erythro-hexopyranosyl)-4'-decyloxybenzene 2 g of tri-O-acetyl-D-glucal and 4 g of dodecyloxybenzene are treated with 2 drops of tin tetrachloride in 50 ml of dry dichloromethane and the mixture is stirred at room temperature for two hours. After adding 2 g of solid sodium carbonate and stirring for 15 min, the mixture is filtered, the dichloromethane is removed in vacuo and the product mixture is taken up in 40 ml of ethanol and 120 ml of ethyl acetate. It is stirred at room temperature under a hydrogen atmosphere for four hours with addition of 10 mg of palladium on active carbon (10%), filtered and concentrated in vacuo. Purification is carried out by column chromatography (silica gel 60, particle size 0.04–0.063, eluent: petroleum ether/ethyl acetate 20:1).

Yield: 28%
Melting point: 53.4° C.

b) Preparation of 1'-(2,3-dideoxy-β-D-erythrohexopyranosyl)-4'-decyloxybenzene

To deacetylate the product from 1a, this is taken up in 50 ml of methanol and treated with 10 mg of sodium methoxide. After stirring at room temperature for 4 hours, the mixture is neutralized using acidic ion exchanger (Amberlite IR 120, H⁺ form) and filtered, and the solvent is removed in vacuo.

Melting point: 103°–106° C.

c) Preparation of (1S,3R,6R,8R)-(4"-decyloxyphenyl)-8-(4'-decyloxyphenyl)-2,4,7-trioxybicyclo[4.4.0]decane 50 mg of 1'-(2,3-dideoxy-β-D-erythrohexopyranosyl)-4'-dodecyloxybenzene are reacted with 5 mg of 4-dodecylbenzaldehyde dimethyl acetal and 5 mg of p-toluenesulfonic acid (monohydrate) in 5 ml of N,N-dimethylformamide in a rotary evaporator at a bath temperature of 60° C. and a pressure of 29–33 mbar. After a reaction time of 1 h, the solvent is removed at a pressure of 8 mbar and a bath temperature of 75° C., the cooled crystalline mass is treated with 5 ml of saturated sodium hydrogen carbonate solution and the solid is filtered off with suction. The residue is washed with sodium hydrogen carbonate solution, water and cold ethanol and recrystallized from ethanol.

Yield: 53%

Phase behavior: K 133.4 $S_A$ 150.2 I

EXAMPLE 2

Preparation of (1S,3R,6R,8R)-3-heptyl-8-(4'-decyloxyphenyl)-2,4,7-trioxybicyclo[4.4.0]decane

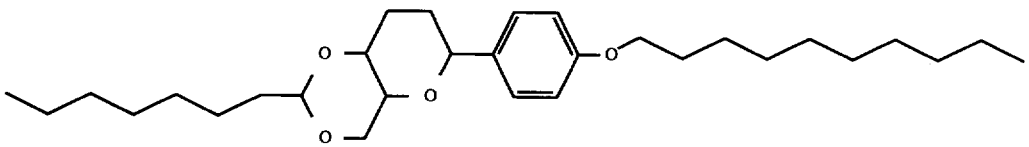

50 mg of 1'-(2,3-dideoxy-β-D-erythrohexopyranosyl)-4'-decyloxybenzene are reacted with 5 mg of octanal dimethyl acetal and 5 mg of p-toluenesulfonic acid (monohydrate) in 5 ml of N,N-dimethylformamide in a rotary evaporator at a bath temperature of 60° C. and a pressure of 29–33 mbar. After a reaction time of 1 h, the solvent is removed at a pressure of 8 mbar and a bath temperature of 75° C., the cooled crystalline mass is treated with 5 ml of saturated sodium hydrogen carbonate solution and the solid is filtered off with suction. The residue is washed with sodium hydrogen carbonate solution, water and cold ethanol and recrystallized from ethanol.

Yield: 65%

Phase behavior: K 75 ($S_A$ 57) I

EXAMPLE 3

Preparation of (1S,3R,6R,8R)-3-(4"-heptyloxyphenyl)-8-(4'-decyloxyphenyl)-3-bora-2,4,7-trioxybicyclo[4.4.0]decane

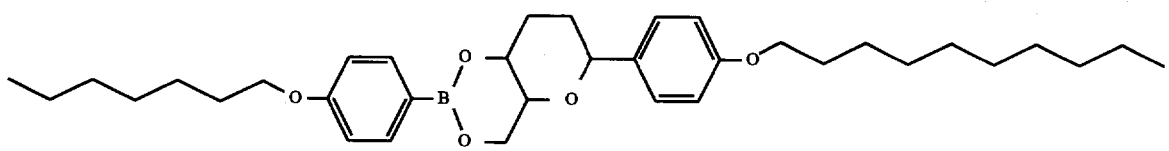

50 mg of 1'-(2,3-dideoxy-β-D-erythrohexopyranosyl)-4'-decyloxybenzene are taken up in 5 ml of toluene with 25 mg of 4-heptyloxyphenylboronic acid. The water formed is removed by azeotropic distillation with toluene in a rotary evaporator in vacuo. The process is repeated three times and the crystalline residue is recrystallized from ethanol.

Yield: 57%
Phase behavior: K 76.8 (S$_c$ 57) S$_A$ 173–174 I
The compounds of Examples 4 to 26 were synthesized in a similar manner to Example 1.
General structure

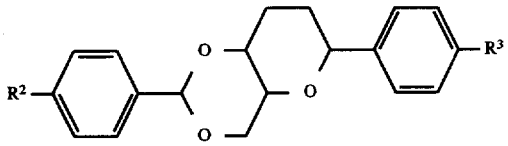

| Example | R$^2$ | R$^3$ | Phase behavior |
|---|---|---|---|
| 4 | CH$_3$O— | —OCH$_3$ | K 195 Ch 206 I |
| 5 | CH$_3$O— | —OC$_6$H$_{17}$ | K 134.7 Ch 151 I |
| 6 | CH$_3$O— | —OC$_{10}$H$_{21}$ | K 133 Ch 146 I |
| 7 | CH$_3$O— | —OC$_{12}$H$_{25}$ | K 130 Ch 140.5 I |
| 8 | C$_6$H$_{13}$O— | —OC$_6$H$_{13}$ | K 159 S$_A$ 164 Ch 165 I |
| 9 | C$_6$H$_{13}$O— | —OC$_8$H$_{17}$ | K 147 S$_A$ 165 I |
| 10 | C$_6$H$_{13}$O— | —OC$_{10}$H$_{21}$ | K 138 S$_A$ 155 I |
| 11 | C$_6$H$_{13}$O— | —OC$_{12}$H$_{25}$ | K 134 S$_A$ 157 I |
| 12 | C$_8$H$_{17}$O— | —OCH$_3$ | K 136 Ch 150 I |
| 13 | C$_8$H$_{17}$O— | —OC$_6$H$_{13}$ | K 148 S$_A$ 163 Ch 169 I |
| 14 | C$_8$H$_{17}$O— | —OC$_8$H$_{17}$ | K 157 S$_A$ 161 I |
| 15 | C$_8$H$_{17}$O— | —OC$_{10}$H$_{21}$ | K 139 S$_A$ 159 I |
| 16 | C$_8$H$_{17}$O— | —OC$_{12}$H$_{25}$ | K 135 S$_A$ 155.5 I |
| 17 | C$_{10}$H$_{21}$O— | —OC$_6$H$_{13}$ | K 141 S$_A$ 158 I |
| 18 | C$_{10}$H$_{21}$O— | —OC$_8$H$_{17}$ | K 138 S$_A$ 157 I |
| 19 | C$_{10}$H$_{21}$O— | —OC$_{12}$H$_{25}$ | K 134 S$_A$ 150 I |
| 20 | C$_{12}$H$_{25}$O— | —OC$_6$H$_{13}$ | K 135 S$_A$ 155 I |
| 21 | C$_{12}$H$_{25}$O— | —OC$_8$H$_{17}$ | K 134 S$_A$ 154 I |
| 22 | C$_{12}$H$_{25}$O— | —OC$_{10}$H$_{21}$ | K 133 S$_A$ 150 I |
| 23 | C$_{12}$H$_{25}$O— | —OC$_{12}$H$_{25}$ | K 137 S$_A$ 146 I |
| 24 | NC— | —OCH$_3$ | K 211 Ch > 215 decomposition |
| 25 | NC— | —OC$_6$H$_{13}$ | K 107 Ch 174 I |
| 26 | NC— | —OC$_8$H$_{17}$ | K 107 Ch 161 I |

The compounds of Examples 27 and 28 were prepared in a similar manner to Example 1:

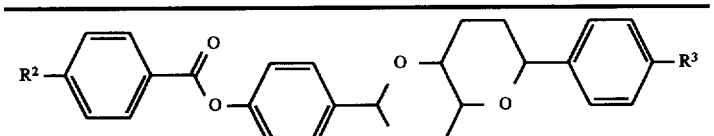

| Example | R$^2$ | R$^3$ | Phase behavior |
|---|---|---|---|
| 27 | C$_{12}$H$_{25}$O— | —OC$_6$H$_{13}$ | K 113 S$_C$ 175 Ch 210 I |
| 28 | C$_6$H$_{13}$O— | —OC$_{12}$H$_{25}$ | K 108 S$_C$ 175 Ch 206 I |

The compound of Example 29 was prepared in a similar manner to Example 1:

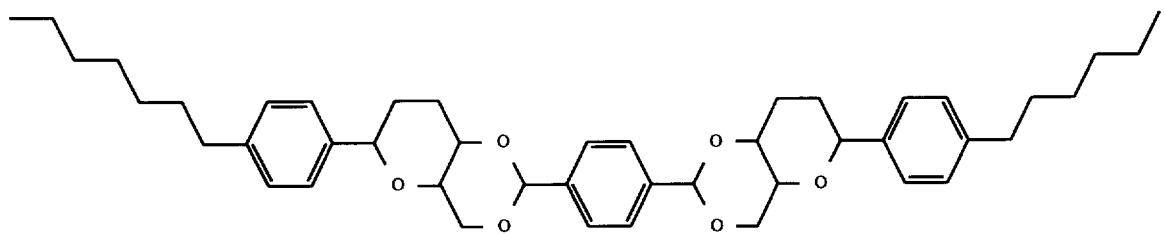

Phase behavior: K 192 S$_c$ 233 Ch>300 decomposition

The compounds of Examples 30 to 46 were prepared in a similar manner to Example 2:

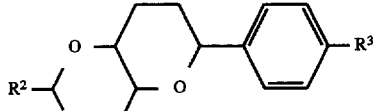

| Example | R$^2$ | R$^3$ | Phase behavior |
|---|---|---|---|
| 30 | C$_5$H$_{11}$— | —OCH$_3$ | K 67 I |
| 31 | C$_5$H$_{11}$— | —OC$_6$H$_{13}$ | K 74 I |
| 32 | C$_5$H$_{11}$— | —OC$_8$H$_{17}$ | K 75 (S$_A$ 60.)3 I |
| 33 | C$_5$H$_{11}$— | —OC$_{10}$H$_{21}$ | K 80 I |
| 34 | C$_5$H$_{11}$— | —OC$_{12}$H$_{25}$ | K 82 (S$_A$ 55) I |
| 35 | C$_7$H$_{15}$— | —OC$_6$H$_{13}$ | K 75 (S$_A$ 59.3) I |
| 36 | C$_7$H$_{15}$— | —OC$_8$H$_{17}$ | K 77 (S$_A$ 64) I |
| 37 | C$_7$H$_{15}$— | —OC$_{12}$H$_{25}$ | K 77 I |
| 38 | C$_9$H$_{19}$— | —OC$_6$H$_{13}$ | K 79 (S$_A$ 59.3) I |
| 39 | C$_9$H$_{19}$— | —OC$_8$H$_{17}$ | K 79 (S$_A$ 64) I |
| 40 | C$_9$H$_{19}$— | —OC$_{10}$H$_{21}$ | K 83 I |
| 41 | C$_9$H$_{19}$— | —OC$_{12}$H$_{25}$ | K 85 I |
| 42 | C$_{11}$H$_{23}$— | —OC$_6$H$_{13}$ | K 77 I |
| 43 | C$_{11}$H$_{23}$— | —OC$_8$H$_{17}$ | K 78 I |
| 44 | C$_{11}$H$_{23}$— | —OC$_{10}$H$_{21}$ | K 79 I |
| 45 | C$_{11}$H$_{23}$— | —OC$_{12}$H$_{25}$ | K 85 I |
| 46 | C$_{11}$H$_{23}$— | —OCH$_3$ | K 57 I |

The compounds of Examples 47 to 68 were prepared in a similar manner to Example 3.

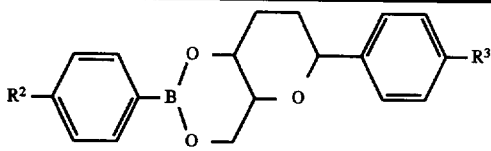

| Example | R² | R³ | Phase behavior |
|---|---|---|---|
| 47 | CH₃O— | —OCH₃ | K 158 Ch 211 I |
| 48 | CH₃O— | —OC₆H₁₃ | K 102 Ch 182 |
| 49 | CH₃O— | —OC₈H₁₇ | K 95 Ch 165 I |
| 50 | CH₃O— | —OC₁₀H₂₁ | K 85 Ch 156 I |
| 51 | CH₃O— | —OC₁₂H₂₅ | K 94 S_A 103 Ch 149 I |
| 52 | C₆H₁₃O— | —OCH₃ | K 92 Ch 176 I |
| 53 | C₆H₁₃O— | —OC₆H₁₃ | K 94 S_A 180 I |
| 54 | C₆H₁₃O— | —OC₈H₁₇ | K 83 S_A 180 Ch > 195 decomposition |
| 55 | C₆H₁₃O— | —OC₁₀H₂₁ | K 76 (S_C 57) S_A 177 I |
| 56 | C₆H₁₃O— | —OC₁₂H₂₅ | K 82 (S_C 44) S_A 168 I |
| 57 | C₈H₁₇O— | —OCH₃ | K 90 S_A 170 I |
| 58 | C₈H₁₇O— | —OC₈H₁₇ | K 85 S_A 178 I |
| 59 | C₈H₁₇O— | —OC₁₀H₂₁ | K 83 S_A 171 I |
| 60 | C₈H₁₇O— | —OC₁₂H₂₅ | K 85 (S_C 52) S_A 178 I |
| 61 | C₁₀H₂₁O— | —OCH₃ | K 93 Ch 163 I |
| 62 | C₁₀H₂₁O— | —OC₈H₁₇ | K 87 S_A 172 I |
| 63 | C₁₀H₂₁O— | —OC₁₀H₂₁ | K 93 S_A 167 I |
| 64 | C₁₀H₂₁O— | —OC₁₂H₂₅ | K 89 S_A 162 I |
| 65 | C₁₂H₂₅O— | —OCH₃ | K 96 Ch 151 I |
| 66 | C₁₂H₂₅O— | —OC₈H₁₇ | K 89 S_A 165 I |
| 67 | C₁₂H₂₅O— | —OC₁₀H₂₁ | K 90 S_A 160 I |
| 68 | C₁₂H₂₅O— | —OC₁₂H₂₅ | K 95 S_A 156 I |

EXAMPLE 69

(1S,6R,8R)-3-(4'-Octoxyphenol)-8-(2"-fluoro-4"-hexoxyphenyl)-2,4,7-trioxa-3-borabicyclo[4.4.0]decane

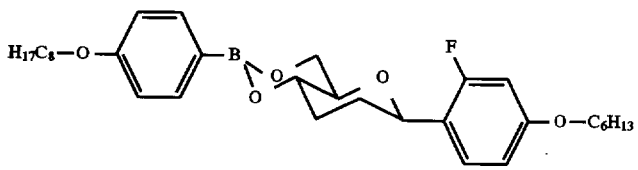

Synthesis of the C-glycoside 1'-[2,3-dideoxy-2,3-didehydro-βD-erythro-hexopyranosyl]-2'-fluoro-4'-hexoxybenzene 3.31 g (16.87 mmol) of 3-fluorohexoxybenzene are added to a solution of 11 mmol (3.06 g) of tri-o-acetal-D-glucal in 50 ml of absolute dichloromethane, and the mixture is treated with 2 drops of tin tetrachloride and stirred at room temperature. The addition of tin tetrachloride can be repeated here, depending on the conversion. After the reaction has taken place, 2 g of solid sodium carbonate are added, and after stirring for a further 15 minutes it is filtered off and the solvent is stripped off on a rotary evaporator.

The residue is taken up in ethanol/ethyl acetate 1:3, treated with 10 mg of palladium on carbon and stirred at room temperature under a hydrogen atmosphere. After the end of the reaction, the catalyst is filtered off and the solvent is removed on a rotary evaporator. The product mixture is separated by column chromatography (eluent petroleum ether 60–70: ethyl acetate 20:1).

For deacetylation, the product is dissolved in 50 ml of methanol, and the solution is treated with a spatula tipful of sodium methoxide and stirred overnight at room temperature. After addition of an acidic ion exchanger (Amberlite® IR 120, H⁺ form) for neutralization, the exchanger is filtered off and the methanol is removed in vacuo.

Yield: 0.219 g, $[\alpha]_D^{20}$=+19.0 (c=0.5, CHCl₃)

The title compound is prepared by conversion of 35 mg (0.11 mmol) of the above C-glycoside using 39.5 mg (0.14 mmol) of 4-octyloxyphenylboronic acid as described in procedure 2.

Yield: 28.4 mg (49%), white solid, $[\alpha]_D^{20}$=+26.8

Phase behavior: K 71.5 Ch 118.6 I

EXAMPLE 70

(1S,6R,8R)-3-(4'-Dodecoxyphenyl)-8-(2"-fluoro-4"-hexoxyphenyl)-2,4,7-trioxa-3-borabicyclo[4.4.0]decane

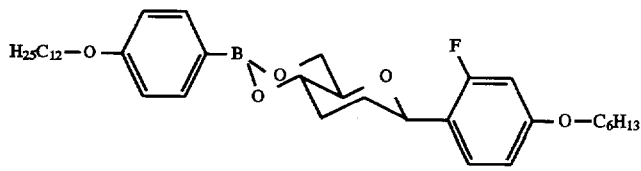

Preparation is carried out as described in Example 69. 27 mg (0.083 mmol) of the C-glycoside from Example 69 were reacted with 40.4 mg (0.12 mmol) of 4-dodecyloxyphenylboronic acid.

Yield: 24.8 mg (50%), white solid, $[\alpha]_D^{20}$=+25.0 (c=0.2, CHCl₃).

Phase behavior: K 71.6 Ch 132.5 I

EXAMPLE 71

(1S,6R,8R)-3-(3'-Fluoro-4'-hexoxyphenyl)-8-(2"-fluoro-4"-hexoxyphenyl)-2,4,7-trioxa-3-borabicyclo[4.4.0]decane

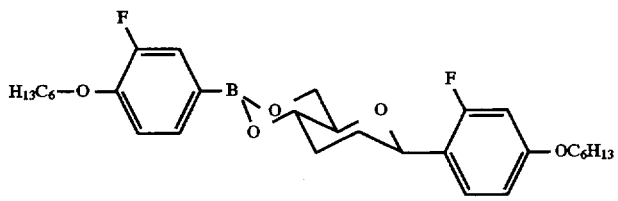

Synthesis of 3-fluoro-4-hexoxyphenylboronic acid 6.7 ml of a 15% strength solution of N-butyllithium in hexane (10.9 mmol) are added dropwise under a nitrogen atmosphere and with continuous stirring at −78° C. to a solution of 3 g (10.9 mmol) of 4-bromo-2-fluorohexoxybenzene in 20 ml of absolute tetrahydrofuran. After stirring at −78° C. for 2.5 hours, the reaction mixture is cautiously treated with 2.4 ml (21.8 mmol) of trimethyl borate. The mixture is stirred overnight and allowed to warm to room temperature during the course of this.

On the next day, the mixture is treated with 9.9 ml of 10% strength hydrochloric acid and stirred at room temperature for a further hour. The organic phase is then separated off, the aqueous phase is extracted twice by shaking with about 50 ml of diethyl ether, and the combined organic phases are washed once with water and then dried with magnesium sulfate. The solvent is stripped off on a rotary evaporator and the residue is recrystallized from an ethanol-water mixture.

Yield: 1.07 g (41%), white crystals.

To prepare the compound of the above formula, 28 mg (0.086 mmol) of the C-glycoside from Example 69 were reacted with 44.3 mg (0.185 mmol) of 3-fluoro-4-hexoxyphenylboronic acid.

Yield: 13.4 mg (29%), white solid, $[\alpha]_D^{20}=+26.0$ (c=0.1, $CHCl_3$).

Phase behavior: K 65.3 Ch 118.0 I

EXAMPLE 72

(1S,3R,6R,8R)-3-(4'-Nitrophenyl)-8-(2"-fluoro-4"-hexoxyphenyl)-2,4,7-trioxabicyclo[4.4.0]decane

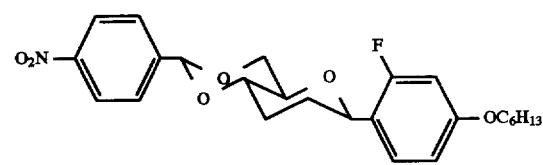

Reaction of 20 mg (0.102 mmol) of 4-nitrobenzaldehyde dimethyl acetal, and 27.8 mg (0.085 mmol) of the C-glycoside from Example 69 as described in procedure 3 affords the compound.

Yield: 25 mg (64%), white solid, $[\alpha]_D^{20}=+34.4$ (c=0.5, $CHCl_3$).

Phase behavior: K 59.6 Q 90.5 D 96.3 Ch 129.9 I.

EXAMPLE 73

(1S,3R,6R,8R)-3-(4'-Cyanophenyl)-8-(2"-fluoro-4"-hexoxyphenyl)-2,4,7-trioxabicyclo[4.4.0]decane

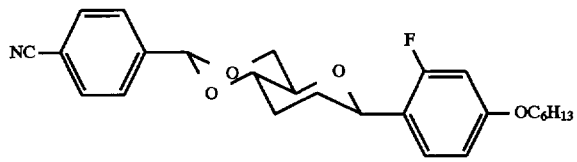

Preparation was carried out as described in Example 72. As described in procedure 3, 40 mg (0.122 mmol) of the C-glycoside from Example 69 were reacted with 40 mg (0.226 mmol) of 4-cyanobenzaldehyde dimethyl acetal.

Yield: 26.3 mg (49%), white solid, $[\alpha]_D^{20}=+30.0$ (c=0.5, $CHCl_3$).

Phase behavior: K 110.8 Ch 154.9 I.

EXAMPLE 74

(1S,3R,6R,8R)-3-(4'-Dodecoxyphenyl)-8-(2"-fluoro-4"-hexoxyphenyl)-2,4,7-trioxabicyclo[4.4.0]decane

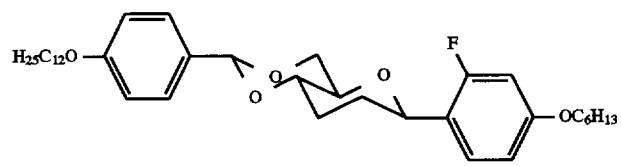

Preparation was carried out as described in Example 72. 28.2 mg (0.086 mmol) of the C-glycoside from Example 69 were reacted with 40 mg (0.12 mmol) of 4-dodecyloxybenzaldehyde dimethyl acetal.

Yield: 34.9 mg (66%), white solid, $[\alpha]^{20}=+20.8$ (c=0.5, $CHCl_3$).

Phase behavior: K 93.6 Ch 106.0 I.

EXAMPLE 75

(1S,3R,6R,8R)-3-(4'-{4"-Hexoxybenzoyloxy}phenyl)-8-(2-fluoro-4-hexoxyphenyl)-2,4,7-trioxabicyclo[4.4.0]decane

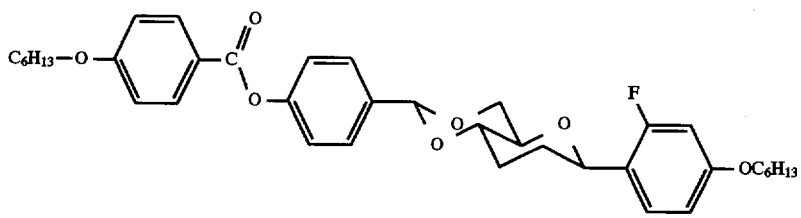

Preparation was carried out as described in Example 72. 31.0 mg (0.095 mmol) of the C-glycoside from Example 69 were reacted with 41.0 mg (0.11 mmol) of 4-(4'-hexoxybenzoyloxy)benzaldehyde dimethyl acetal.

Yield: 39.9 mg (66%), white solid, $[\alpha]_D^{20}=+27.0$ (c=0.5, CHCl$_3$).

Phase behavior: K 97.0 Ch 250.0 I.

EXAMPLE 76
(1S,6R,8R)-3-(3'-Fluoro-4'-hexoxyphenyl)-8-(4"-octoxyphenyl)-2,4,7-trioxa-3-borabicyclo[4.4.0]decane

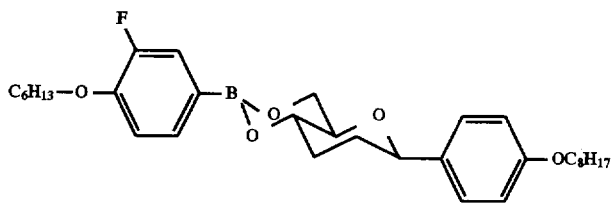

Preparation of this compound was carried out according to general procedure 2. 30 mg (0.085 mmol) of 1-[2,3-dideoxy-2,3-didehydro-β-D-erythrohexapyranosyl]-4'-octoxybenzene were reacted with 43 mg (0.179 mmol) of the boronic acid indicated in Example 71.

Yield: 29.0 mg (60%), white solid, $[\alpha]_D^{20}=+19.4$ (c=0.5, CHCl$_3$).

Phase behavior: K 66.7 (S$_c$* 52.4) S$_A$ 163.7 I.

EXAMPLE 77
(1S,6R,8R)-3-(3'-Fluoro-4'-hexoxyphenyl)-8-(4"-decoxyphenyl)-2,4,7-trioxa-3-borabicyclo[4.4.0]decane

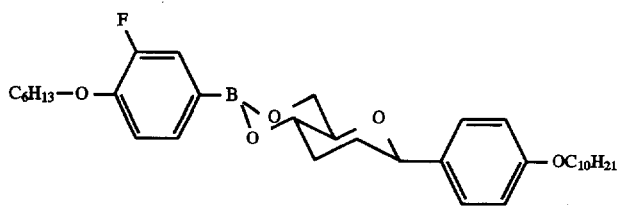

Preparation was carried out as described in Example 76. 30 mg (0.078 mmol) of 1'-[2,3-dideoxy-2,3-didehydro-β-D-erythrohexapyranosyl]-4'-decyloxybenzene were reacted with 39.5 mg (0.164 mmol) of the boronic acid indicated in Example 71.

Yield: 23.5 mg (50%), white solid, $[\alpha]_D^{20}=+17.5$ (c=0.2, CHCl$_3$).

Phase behavior: K 67.7 (S$_c$* 39.3) S$_A$ 158.7 I.

EXAMPLE 78
(1S,6R,8R)-3-(3'-fluoro-4'-Hexoxyphenyl(-8-(4"-dodecoxyphenyl)-2,4,7-trioxa-3-borabicyclo[4.4.0]decane Preparation was carried out as described in Example 76. 32 mg (0.078 mmol) of 1-[2,3-dideoxy-2,3-didehydro-β-D-erythrohexapyranosyl]-4-dodecyloxybenzene were reacted with 50 mg (0.208 mmol) of the boronic acid indicated in Example 71.

Yield: 31.5 mg (65%), white solid, $[\alpha]_D^{20}=+15.8$ (c=0.5, CHCl$_3$).

Melting point: 69.0° C.

EXAMPLE 79
(1S,6R,8R)-3-(3'-Fluoro-4'-hexoxyphenyl)-8-(4''-tetradecoxyphenyl)-2,4,7-trioxa-3-borabicyclo[4.4.0]decane Preparation was carried out as described in Example 76. 32 mg (0.073 mmol) of 1-[2,3-dideoxy-2,3-didehydro-β-D-erythrohexapyranosyl]-4-tetradecyloxybenzene were reacted with 50 mg (0.208 mmol) of the boronic acid indicated in Example 71.

Yield: 32.2 mg (67%), white solid, $[\alpha]_D^{20}=+16.8$ (c=0.5, CHCl$_3$).

Phase behavior: K 73.4 (S$_c$* 28.0) S$_A$ 150.7 I.

EXAMPLE 80
2,4-Bis{(1S,3R,6R,8R)-8-(2''-fluoro-4''-hexoxyphenyl)-2,4,7-trioxabicyclo[4.4.0]decyl}benzene Preparation was carried out as described in procedure 3. 26.4 mg (0.081 mmol) of the glycoside indicated in Example 69 were reacted with 8.6 mg (0.038 mmol) of terephthalaldehyde tetramethyl acetal.

Yield: 23.3 mg (38%), white solid, $[\alpha]_D^{20}=+43.0$ (c=0.1, CHCl$_3$).

Phase behavior: K 143.9 Ch 280.0 I.

We claim:

1. A chiral compound of the general formula I $$A-Y^1-M_n-Z-Y^1-M_n-A \qquad I$$

where

Z is a radical of the formula and where the radicals

A independently of one another are C$_1$- to C$_{20}$-alkyl which may be substituted by fluorine, chlorine, bromine or cyano and may be interrupted by O, S, NH, NCH$_3$, COO or OCO, M independently of one another are a mesogenic group consisting of an aromatic or aliphatic ring system of the general formula II $$(Z^1-Y^1-)_m- \qquad II$$

where the radicals

Y$^1$ independently of one another are a direct bond, O, COO, OCO, CH$_2$O, OCH$_2$, CH=N or N=CH, $Z^1$ independently of one another are p-phenylene, 1,3,4-thiadiazol-2,5-ylene or 2,5-pyrimidylene which may be substituted by fluorine, chlorine, bromine, iodine, cyano, hydroxyl, methoxy or methyl, and m is an integer from 1 to 3,
and n independently of one another are 0 or 1 with the proviso that one n is other than 0.

2. A compound as claimed in claim 1, where the radicals A independently of one another are $C_1$- to $C_{12}$-alkyl which may be interrupted by O, COO or OCO.

3. A compound as claimed in claim 1, where the radicals Y' independently of one another are a direct bond, O, COO or OCO.

4. A compound as claimed in claim 1, where the radicals

A independently of one another are $C_1$- to $C_{12}$-alkyl which may be interrupted by O, COO or OCO and Y' independently of one another are a direct bond or O, COO or OCO.

5. A liquid-crystalline medium, comprising the compound of claim 1.

6. A display, comprising the liquid-crystalline media of claim 5.

* * * * *